US010519173B2

(12) United States Patent
Murray et al.

(10) Patent No.: US 10,519,173 B2
(45) Date of Patent: Dec. 31, 2019

(54) PROCESS FOR THE REMOVAL AND RETURN OF A CATALYST TO A LIQUID PHASE MEDIUM

(71) Applicant: PHOSPHONICS LTD, Oxford (GB)

(72) Inventors: Paul Murray, Yate (GB); Robin Wilkes, Oxford (GB); Christopher North, Oxford (GB)

(73) Assignees: PHOSPHONICS LTD, Oxford, Oxfordshire (GB); Paul Murray, Yate (GB)

( * ) Notice: Subject to any disclaimer, the term of this patent is extended or adjusted under 35 U.S.C. 154(b) by 0 days.

(21) Appl. No.: 14/647,919

(22) PCT Filed: Nov. 28, 2013

(86) PCT No.: PCT/EP2013/074974
§ 371 (c)(1),
(2) Date: Jun. 12, 2015

(87) PCT Pub. No.: WO2014/083109
PCT Pub. Date: Jun. 5, 2014

(65) Prior Publication Data
US 2015/0299229 A1 Oct. 22, 2015

(30) Foreign Application Priority Data
Nov. 28, 2012 (GB) .................................... 1221402.9

(51) Int. Cl.
| | | |
|---|---|---|
| *C07F 7/10* | (2006.01) | |
| *C08G 77/385* | (2006.01) | |
| *C08G 77/388* | (2006.01) | |
| *C08G 77/392* | (2006.01) | |
| *C08G 77/395* | (2006.01) | |
| *B01J 31/06* | (2006.01) | |
| *B01J 31/16* | (2006.01) | |
| *B01J 31/24* | (2006.01) | |
| *C07F 7/08* | (2006.01) | |
| *C07F 17/02* | (2006.01) | |

(52) U.S. Cl.
CPC .............. *C07F 7/10* (2013.01); *B01J 31/069* (2013.01); *B01J 31/1633* (2013.01); *B01J 31/1658* (2013.01); *B01J 31/2409* (2013.01); *C07F 7/0834* (2013.01); *C07F 17/02* (2013.01); *C08G 77/385* (2013.01); *C08G 77/388* (2013.01); *C08G 77/392* (2013.01); *C08G 77/395* (2013.01); *B01J 2231/321* (2013.01); *B01J 2231/42* (2013.01); *B01J 2231/4211* (2013.01); *B01J 2531/0205* (2013.01); *B01J 2531/16* (2013.01); *B01J 2531/80* (2013.01); *B01J 2531/824* (2013.01); *B01J 2531/842* (2013.01); *B01J 2531/847* (2013.01); *Y02P 20/588* (2015.11)

(58) Field of Classification Search
CPC ........................................................ C07F 7/00
USPC ........................................................ 556/14
See application file for complete search history.

(56) References Cited

U.S. PATENT DOCUMENTS

| | | |
|---|---|---|
| 2005/0029195 A1 | 2/2005 | Gibson et al. |
| 2009/0098082 A1 | 4/2009 | Wilson et al. |
| 2009/0220449 A1* | 9/2009 | Wilson ................... C08G 77/28 424/78.37 |
| 2010/0290962 A1 | 11/2010 | Wilson et al. |

FOREIGN PATENT DOCUMENTS

| | | |
|---|---|---|
| WO | 2006/013080 A1 | 2/2006 |
| WO | 2007/006569 A1 | 1/2007 |
| WO | 2011/128061 A1 | 10/2011 |
| WO | 2012/095307 A1 | 7/2012 |

OTHER PUBLICATIONS

International Search Report PCT/EP2013/074974.*
Written Opinion of the ISA; International application No. PCT/EP2013/074974.*
Bedford et al. (2001) "Silica-supported imine palladacycles—recyclable catalysts for the Suzuki reaction?" Journal of Organometallic Chemistry. 633(1-2):173-181.
Burguete et al. (2010) "Pd catalysts immobilized onto gel-supported ionic liquid-like phases (g-SILLPs): A remarkable effect of the nature of the support," Journal of Catalysis. 269(1):150-160.
Gomes et al. (2006) "Sulfonated silica-based electrolyte nanocomposite membranes," Journal of Polymer Science Part B: Polymer Physics. 44(16):2278-2298.
Gruttadauria et al. (Jul. 24, 2013) "Release and catch' catalytic systems," Green Chemistry. 15(10):2608-2618.
(Continued)

*Primary Examiner* — Brandon J Fetterolf
*Assistant Examiner* — Kofi Adzamli
(74) *Attorney, Agent, or Firm* — Lathrop Gage LLP; Brian C. Trinque; Benjamin A. Vaughan

(57) ABSTRACT

A process for the selective removal of a component from a liquid phase and subsequently returning the component to a liquid phase is disclosed. A novel compound of formula (I) [SUP]-[[L]-[G]]a (I) in which L is a linking group, G is an aryl group having a leaving group LG selected from Cl, Br, I, sulfonate such as triflate, a diazo group, a nitrile, an ester and an alkoxy group and substituent Q is selected from H, NR2, OR, CO2R, F, Cl, NO2 CN and SUP is a support having a plurality of groups -[L]-[G] bound to the support is contacted with the liquid phase to bind the component to the compound I thereby forming a captured component which is separated from and may be returned to the liquid phase. The compound I is especially useful in binding homogeneous catalysts to remove it from a reaction medium and selectively returning the catalyst to the reaction medium at a later stage. The compound is particularly useful for cross-coupling reactions, for example in Suzuki reactions.

5 Claims, No Drawings

(56) References Cited

OTHER PUBLICATIONS

Harned (2012) "Cross-Coupling Reactions," Chemistry 8322/4322: Lecture Notes. Regents of the University of Minnesota. Accessible on the Internet at URL: http://www.chem.umn.edu/groups/harned/classes/8322/lectures/8CrossCoupling.pdf. [Last Accessed Aug. 28, 2015].

Hayashi (1999) "Cross-Coupling Reactions," Ch. 25 In; Comprehensive Asymmetric Catalysis. Eds.: Jacobsen et al. Springer-Verlag. Berlin, Heidelberg.

Kawabata et al. (1981) "Sirotherm catalysis. Homogeneously catalyzed carbonylations using polymer-bound rhodium complexes," Jornal of Molecular Catalysis. 12(1):113-119.

Ohtaka (Jan. 1, 2011) "Recovery of In Situ-Generated Pd Nanoparticles with Linear Polystyrene," Green and Sustainable Chemistry. 1(2):19-25.

Ohtaka et al. (May 16, 2013) "A Recyclable 'Boomerang' Linear Polystyrene-Stabilized Pd Nanoparticles for the Suzuki Coupling Reaction of Aryl Chlorides in Water," ChemCatChem. 5(8):2167-2169.

Phan et al. (2006) "On the Nature of the Active Species in Palladium Catalyzed Mizoroki—Heck and Suzuki—Miyaura Couplings—Homogeneous or Heterogeneous Catalysis, A Critical Review," Advanced Synthesis and Catalysis. 348(6):609-679.

Yu et al. (2005) "Evidence that SCS Pincer Pd(II) Complexes are only Precatalysts in Heck Catalysis and the Implications for Catalyst Recovery and Reuse," Advanced Synthesis and Catalysis. 347(1):161-171.

Zhao et al. (2000) "Heck Reactions of Iodobenzene and Methyl Acrylate with Conventional Supported Palladium Catalysts in the Presence of Organic and/and Inorganic Bases without Ligands," Chemistry—A European Journal. 6(5):843-848.

International Preliminary Report on Patentability corrresponding to International Patent Application No. PCT/EP2013/074974, dated Jun. 2, 2015.

International Search Report with Written Opinion corrresponding to International Patent Application No. PCT/EP2013/074974, dated Sep. 17, 2014.

Search Report corresponding to Great Britain Patent Application No. 1221402.9, dated Jun. 7, 2013.

* cited by examiner

PROCESS FOR THE REMOVAL AND RETURN OF A CATALYST TO A LIQUID PHASE MEDIUM

RELATED APPLICATIONS

This application is a 35 U.S.C. § 371 filing of International Application No. PCT/EP2013/074974, filed Nov. 28, 2013, which claims priority to Great Britain Patent Application No. 1221402.9, filed Nov. 28, 2012, each of which is incorporated herein by reference in its entirety.

The invention relates to a process for the removal and return of a catalyst to a liquid phase medium and to a novel compound having pendant functional groups bound to a support, for example a new organopolysiloxane, and its use in selectively binding and releasing a species, for example a catalyst. The invention also relates to a process for reusing a catalyst for successive reactions and to a process for producing a product by a catalysed reaction in which the catalyst, which may have associated ancillary ligands, is selectively bound so as to remove it from a reaction environment. The invention may also involve a purification step where excess reagent may in addition to the catalyst be removed by the novel compound. The catalyst may subsequently be released back into the reaction environment for further use with or without excess reagent. The invention particularly relates to a process for the formation of a new covalent bond between a carbon atom and another atom selected from carbon, nitrogen, oxygen or other heteroatom through a homogeneously catalysed process in which the catalyst may be selectively removed and returned to the reaction. Such reactions are sometimes referred to as cross-coupling reactions. The invention also relates to a process for the production of the organopolysiloxane.

Functionalised materials are employed in many different applications including as catalysts in solution phase synthesis and solid phase synthesis, solid phase extraction, as catalyst supports, in product purification and in the immobilisation of bio-molecules. Typically, functionalised materials employed in such applications require excellent physical and chemical stability over a wide range of operating conditions, broad solvent applicability, fast kinetics and functional groups with high intrinsic activity and selectivity for the desired application. In addition, the preparation of such functionalised materials is desirably relatively simple and from readily available reagents in order for the synthesis to be economic and suitable for commercial scale production.

Functionalised materials are also known for use in removing a component for example a catalyst, from a reaction medium. The removed, bound component may then be subjected to a further process for example recovery or recycling of the component for further use. Known treatments to recover the desired material include separation techniques, chemical regeneration and incineration. These treatments may be complex, expensive, inefficient or ineffective due to recycling in some cases being especially difficult.

In the chemical and pharmaceutical industries, recovery and reuse of catalysts especially homogeneous catalysts from a reaction medium is particularly important to ensure residual levels of the catalyst in the reaction medium are kept to acceptably low levels so as not to be carried through in the synthesised product. Recovery and reuse of the catalyst provides advantage in managing operating costs, particularly as the active catalyst can contain both expensive metal and ligand components, and process efficiency and in reducing waste products. In pharmaceutical, agrochemical and fine chemical manufacturing regulatory or safety issues may arise requiring levels of metals from catalysts to be below certain levels. Various methods are known for recovery of catalysts and catalyst components including phase separation methods, separation methods in which functionalised ligands are employed to provide separation in homogeneous reaction media, for example sulfonated, quaternary ammonium salts where aqueous solubility is required and fluorous tags for fluorous liquid/liquid extraction. Another separation method involves the solid support of ligands onto magnetic nanoparticles. Membrane separation technology has also been employed. These recovery methods tend to be relatively complex and costly and the catalyst is removed from the reaction process for treatment "off-line" or separately from the reaction process, necessitating additional charges of catalyst to allow the reaction process to continue to be operated while the spent catalyst is recovered and treated for reuse.

Efficient recovery of metals is important due to the intrinsic value of the metal, limited availability of certain metals, improving product purity and due to environmental considerations for example reducing the requirement for waste treatment or management. There remains a need for materials which are able to recover metals or other species containing metals for example catalysts. Catalysts containing metals find widescale application in the chemical and pharmaceutical sectors and are employed in a wide range of reactions including for example alpha arylation, amidation, amination, esterification, etherification, cyanation, and carbonylation and examples of metals used in catalysis include transition metals, for example platinum, palladium, rhodium, ruthenium, iridium, nickel, copper and iron.

Homogeneous catalysis in organic synthesis provides benefits such as high activity, rapid kinetics however catalyst recovery and reuse may be problematic or in certain circumstances not possible. For potential reuse purposes, it is especially important that any work-up processes ensure the catalyst is retained in its active form. Heterogeneous catalysis provides rapid purification and workup and the catalyst may be recycled albeit with certain limitations, including reduced activity and slower kinetics, as mentioned above.

The present invention aims to solve the problem of how to provide high catalytic activity and rapid kinetics in combination with efficient work-up and purification of the reaction product alongside efficient catalyst use and reuse. We have now found that a catalyst may be selectively removed from a reaction medium for a period of time and then returned to the same or a different reaction medium affording the benefits of employing homogeneous catalysis in a reaction for example an organic synthesis, whilst gaining the benefits of a heterogeneous catalyst system, for example easier purification, whilst regenerating or recovering the catalyst.

In a first aspect the invention provides a process for the selective removal of a component from a liquid phase medium and subsequently returning the component to a liquid phase medium comprising contacting a compound of formula I below with the liquid phase medium to bind the component to the compound I thereby forming a bound component, separating the bound component and the medium, subsequently returning the bound component to the medium and treating the bound component so as to release the component from compound I wherein the compound I is of formula:

$$[SUP]\text{-}[[L]\text{-}[G]]_n \quad (I)$$

wherein:
L is a group linking G to SUP- and is selected from:
i) —(CH$_2$)$_h$[S(O)$_d$]$_m$(CHD)$_n$Z$_m$((CH$_2$)$_n$Y(CH$_2$)$_n$)$_m$ where D is selected from H, CN, OH, —C(O)OR, —C(O)NR$_2$— C(O)OG, —CONRG and Y is selected from O, NR, S(O)$_d$, CO, CO$_2$, —NRCOZ$_m$—, —Z$_m$CONR—, —C=N—, a heterocyclic ring where Z is independently O, S, NR; and
ii) —(CH$_2$)$_h$ P(=O)(OR)O—(CH$_2$)$_h$
and wherein d is independently 0 to 2, preferably 0, h is from 0 to 15, more preferably from 0 to 12, especially 0 to 4, optimally 2 or 3, m is independently 0 or 1 and n is independently 0 to 4 and R is independently selected from H or a C$_{1-12}$ alkyl group, preferably C$_{1-6}$alkyl group for example methyl or ethyl, or a phenyl group; or L is not present and G is linked directly to SUP;
G is selected from an alkyl group, an aryl group, a heterocyclic group and a heteroaryl group, preferably an aromatic group or a heteroaromatic group having one or two aromatic rings;
wherein the group G has
i) a leaving group LG and is preferably selected from Cl, Br, I, a pseudohalide; and
ii) substituent Q selected from H, NR$_2$, N$^+$R$_3$, —N(R)CO$_2$H, —N=CR$_2$, OR, —O$^+$(R)SiR$_3$, CO$_2$R, CO$_2$$^-$, —CONR$_2$, —NRC(O)R, F, Cl, NO$_2$, CN and a ring formed between group Q and a part of group L, for example —O—C(O)— where the ether oxygen is bound to G and the carbonyl group is a part of group L;
SUP is a support, preferably a chemically inert support, having a plurality n of groups -[L]-[G] bound to the support.
Preferably, the support comprises a plurality of groups [L]-[G] at such a level as to provide a loading of 0.1 to 5, preferably 0.5 to 2 mmol of group [L]-[G] per gram of support.
The term "leaving group" refers to a group which is capable of being substituted under certain conditions and includes Cl, Br, I, OH and pseudohalides. The term "pseudohalide" is well known in the chemical field and is employed herein in its conventional sense to mean a substituent that exhibits significant similarity to the halogens as regards their properties as leaving substituents and includes sulfonates including triflate, a diazo group, a nitrile, an ester and an alkoxy group. The leaving group LG may be located at any location on the group [G] provided it is sufficiently labile to act as a leaving group in the particular use. Preferably, the leaving group LG is located at a para position relative to the bond between groups [G] and [L].
Preferably, the heteroaromatic group is selected from:

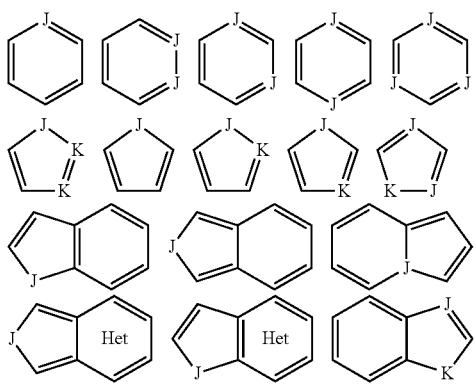

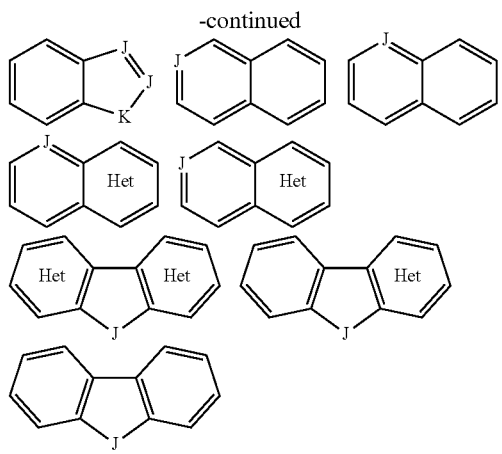

Examples of suitable heterocyclic groups include:

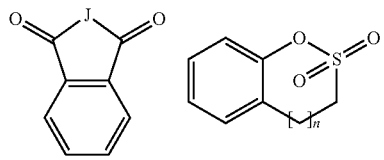

wherein J and K are independently selected from, when divalent, O, NR, S and CH$_2$ or, when trivalent, =N—, =CH— and wherein HET signifies a heteroatom-containing species being present within the ring encircling HET. In this case, the G group is suitably linked to the L group via a carbon atom in the G group. The group Q may be located at any position in the heteroaromatic group.

The invention provides a process for selectively removing and reintroducing a catalyst to a reaction medium containing the catalyst comprising removing the catalyst from the reaction medium by contacting a compound of formula I with the reaction medium so as to bind the catalyst to the compound of formula I, treating the bound catalyst such that the catalyst is released in its active first form to the same or a different reaction medium.

Preferably the support SUP is selected from a silica and alumina. A silica support is especially preferred. A silica or alumina support will have some unreacted hydroxyl groups and these may be end-capped in part or whole, preferably with an alkyl group, more preferably a C$_{1-6}$ alkyl group, for example propyl. The support SUP suitably comprises repeat units linked together to form a cross-linked matrix, for example a silica or alumina matrix and at least some of the silicon atoms or aluminium atoms have the groups -[L]-[G] bound to them. Where the support SUP comprises a polymer, the polymer is suitably selected from the group consisting of polystyrene, polyethylene glycol, poly(vinylpyrrolidine), poly(ethylene oxide), poly(vinyl chloride), polyethylenimine, polyacrylonitrile, poly(ethyleniminodiacetic acid), polyphazene, polysiloxanes, polyacrylamide, or a dendrimeric polymer, including block or copolymers thereof. The functional groups may be attached to the polymer chain by copolymerization with one or more monomers. Alternatively, the functionalised polymer may be prepared by functionalising the already formed polymer, for example as shown in Bergbreiter, Using Soluble Polymers to Recover Catalysts and Ligands, Chem. Rev. 102(10), 3345-3384 (2002), which is incorporated by reference. The functionalised polymer may be cross-linked or uncrosslinked. In one aspect, the polymer is cross-linked and has a crosslinker ratio ranging from 8 to 12 in moles of monomer to moles of crosslinking monomer. Exemplary classes of polymer backbones are disclosed in Bergbreiter, Using Soluble Polymers to Recover Catalysts and Ligands, Chem. Rev. 102(10) 3345-3384 (2002), which is incorporated by reference.

Preferably, the support SUP comprises silica and group G is an optionally substituted halo-aryl, heteroaryl or alkyl group. Where a silicon or aluminium atom does not have the group -[L]-[G], they suitably have all valencies satisfied by silicate or aluminate oxygen atoms. The silicate oxygen atoms or aluminate oxygen atoms are suitably saturated by: silicon or aluminium atoms of other repeat units;
hydrogen;
a linear or branched $C_{1-12}$-alkyl group;
an end group of formula $R^8{}_3M^1O_{1/2}$, a cross-linking bridge member or a polymer chains of formula $R^8{}_qM^1(OR^9)_jO_{k/2}$ or $Al(OR^9)_{3-p}O_{p/2}$ or $R^8Al(OR^9)_{2-r}O_{r/2}$ where $M^1$ is Si or Ti;
$R^8$ and $R^9$ are independently selected from a linear or branched $C_{1-40}$ alkyl group an aryl group and a $C_{1-40}$-alkylaryl group; k is an integer from 1 to 3, q is an integer from 1 to 2 and j is an integer from 0 to 2 such that j+k+q=4, where; p is an integer from 1 to 3; and r is an integer from 1 to 2; and
other known oxo metal bridging systems where the metal is zirconium, boron, magnesium, iron, nickel or a lanthanide.

The component may be removed from a first liquid phase medium and returned to a second liquid phase medium but suitably the first and second liquid phase media are the same. More preferably the liquid phase medium is a reaction medium and the component participates in a chemical reaction in the medium. Preferably the component comprises a catalyst comprising a metal, for example, platinum, palladium, rhodium, ruthenium, iridium, nickel, copper and iron.

The bound component may be separated from the first liquid phase medium by any suitable method, for example physical separation. The bound component may be released from the compound I by treating the bound component chemically, for example by contact with a compound, or physically, preferably by changing a reaction condition for example temperature, pressure or pH, so as to cause a shift in an equilibrium whereby the bound component is released from the compound I into the second liquid phase medium.

In a second aspect, the invention provides a homogeneously catalysed process for the formation of a covalent bond between a carbon atom and a second carbon atom or a heteroatom, for example nitrogen and oxygen in a reaction medium comprising a catalyst wherein the catalyst is selectively removed and returned to the reaction medium, the process comprising contacting a catalyst CAT with a compound of formula II R"-LG to produce an organometallic species of formula III R"-CAT-LG, treating -III with a compound IV R""[MET]$_e$[X"]$_f$ to replace the leaving group LG with a group R"" to form compound V R"-R"" and release the catalyst CAT into the reaction medium wherein R" and R"" are independently selected from aryl, heteroaryl, benzyl, alkyl, vinyl, allyl, alkynyl, acyl, sulfonyl—or heterocyclic moiety, LG is a leaving group as hereinbefore defined, [MET] is selected from a metal capable of use in an organometallic species, preferably Mg or Zn, and boron, X" is selected from halogen, preferably F, Cl or Br, and OH, e is 0 or 1 and f is an integer from 1 to 4, preferably 1 and 2, selected to satisfy the free valencies of species R""[MET]$_e$.

The catalyst CAT may be any metallic element or compound containing metal. In a preferred embodiment, the catalyst comprises a metal species comprising a metal selected from Pd, Ni, Fe, Cu, Pt, Rh, Ru and Ir.

Preferably R" and R"" are independently selected from aryl, heteroaryl, alkyl and a heterocyclic moiety.

Preferably the compound IV R""[MET]$_e$[X"]$_f$ is selected from R""LiX", a Grignard reagent of formula R""MgX" where X" is Cl or Br, R"""B(X")$_2$, and R""ZnCl.

Advantageously, the invention enables a catalyst employed in a homogeneous reaction to be bound and removed from the reaction medium to enable recycling and extend its operating life and to provide flexibility of usage of the catalyst for different batches of the same reaction or for different reactions without needing to treat or regenerate the catalyst "off-line". The homogeneous reaction may be continuous and the invention may remove the catalyst for treatment, for example to a zone in which the catalyst is separate from the reaction process, while the reaction process continues.

In a third aspect, the invention provides a novel compound of formula I.

The compound I is preferably a novel organopolysiloxane containing a silica support and an aryl, heteroaryl, heterocyclic or alkyl moiety connected via a linking group.

In a fourth aspect, the invention provides a compound of formula (VI):

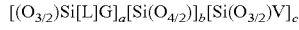

wherein:
L is a group linking G to $(O_{3/2})$Si— and is selected from:
i) —$(CH_2)_h[S(O)_d]_m(CHD)_nZ_m((CH_2)_nY(CH_2)_n)_m$ where D is selected from H, CN, OH, —C(O)OR, —C(O)NR$_2$ —C(O)OG, —CONRG and Y is selected from O, NR, $S(O)_d$, CO, CO$_2$, —NRCOZ$_m$—, —Z$_m$CONR—, —C=N—, a heterocyclic ring, for example succinimide, where Z is independently O, S, NR; and
ii) —$(CH_2)_h$ P(=O)(OR)O—$(CH_2)_h$
and wherein d is independently 0 to 2, preferably 0, h is from 0 to 15, more preferably from 0 to 12, optimally 0 to 4, especially 2 or 3, m is independently 0 or 1 and n is independently 0 to 4 and R is independently selected from H or a $C_{1-12}$ alkyl group, preferably $C_{1-6}$ alkyl group for example methyl or ethyl, or a phenyl group;
G is an alkyl group, preferably selected from $C_{1-12}$ alkyl group and more preferably a $C_{1-6}$ alkyl group, an aryl group, a heterocyclic group or a heteroaryl group, preferably an aromatic group or a heteroaromatic group having one or two aromatic rings, selected from:

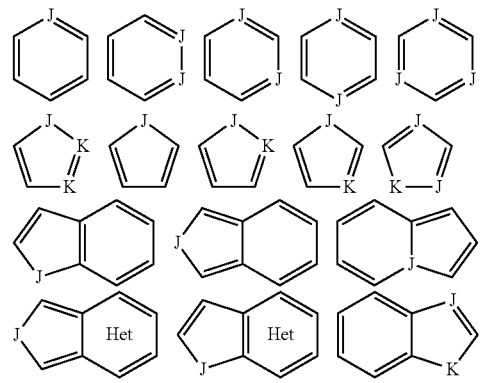

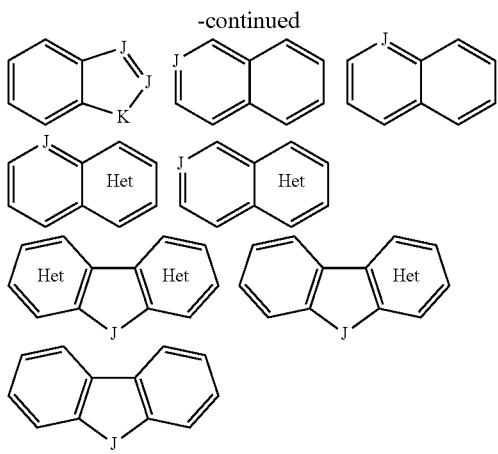

Examples of suitable heterocyclic groups include:

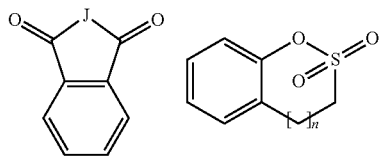

wherein J and K are independently selected from, when divalent, O, NR, S and $CH_2$ or, when trivalent, =N—, =CH— and wherein HET signifies a heteroatom-containing species being present within the ring encircling HET;
wherein LG is a leaving group and is preferably selected from Cl, Br, I and a pseudohalide, a sulfonate, including triflate, a nitrile, a diazo group, an ester and an alkoxy group and substituent Q is selected from H, $NR_2$, $N^+R_3$, —N(R)$CO_2H$, —N=$CR_2$, OR, $O^+(R)SiR_3$, $CO_2R$, $CO_2^-$, —$CONR_2$ —NRC(O)RF, Cl, $NO_2$, CN and a ring formed between group Q and a part of group L, for example O—C(O)— where the ether oxygen is bound to G and the carbonyl group is a part of group L;
V is an optionally substituted $C_{1-12}$ alkyl, $C_{2-12}$ alkenyl or $C_{2-12}$ alkynyl group or an aryl group or $C_{1-12}$ alkylaryl sulfide, sulfoxide, sulfone, amine or a polyalkyl amine or phosphine or other phosphorous containing group;
the free valences of the silicate oxygen atoms are saturated by one or more groups selected from:
silicon atoms of other groups of Formula VI;
hydrogen;
a linear or branched $C_{1-12}$ alkyl group;
an end group of formula $R^8_3M^1O_{1/2}$, a cross-linking bridge member or a polymer chains of formula $R^8_qM^1(OR^9)_jO_{k/2}$ or $Al(OR^9)_{3-p}O_{p/2}$ or $R^8Al(OR^9)_{2-r}O_{r/2}$ where $M^1$ is Si or Ti;
$R^8$ and $R^9$ are independently selected from a linear or branched $C_{1-40}$ alkyl group an aryl group and a $C_{1-40}$ alkylaryl group; k is an integer from 1 to 3, q is an integer from 1 to 2 and j is an integer from 0 to 2 such that j+k+q=4; p is an integer from 1 to 3; and r is an integer from 1 to 2; and
other known oxo metal bridging systems where the metal is zirconium, boron, magnesium, iron, nickel or a lanthanide; and
a, b and c are integers, a is greater than 0 and a, b and c are such that when b is 0 the ratio of a:c is from 0.001 to 1000 and when b is 1 or more the ratio of a:b is from 0.001 to 1000.

Advantageously the organopolysiloxane of the invention enables a component, for example a catalyst to be captured thereby removing it from a reaction medium and, upon contact with a further species or change in reaction conditions, allows the catalyst to be released back to the reaction medium. The catalyst may be bound to the organopolysiloxane and be released whilst being released to the reaction medium to act as a catalyst in a second reaction. The second reaction may involve the same substrates or different substrates.

The compound of formula (VI) is a functionalised silica and advantageously does not swell to any appreciable degree in the reaction medium and therefore allows the compound VI to be used under continuous processing conditions by employment in a cartridge for contact with the reaction medium. The compound of formula VI is also chemically and physically stable and may be produced to a high level of purity enabling the compound VI to be employed in processes for the production of pharmaceuticals, agrochemicals or the like where high levels of quality control may be necessary. Polystyrene based materials may be limited to use in certain solvents and not used at temperatures above about 80° C.

Organopolysiloxane compounds of Formula VI may be used in a wide range of solvents and are not limited in their application to reaction temperatures below 80° C.

Other advantages include fixed and rigid structures, insolubility in organic solvents, high resistance to ageing, relatively easy purification and high reusability. In addition the processes for the preparation of compounds of Formula VI are flexible, allowing a wide range of functionalised materials with different linking groups L or groups G with substituents Q and LG to be made from a small number of common intermediates.

The porosity of the compound of formula VI may be varied from micro to macro porous and the loading of the functional groups as well as the other substituents in the fragment VI may be varied as needed. Compounds of Formula VI have the added advantage of their respective functional groups being firmly attached to a very stable and inert medium.

Preferably linker group L is a divalent group linking G to $(O_{3/2})Si$— and is selected from:
i) —$(CH_2)_h(CHD)_n(Y)_m(CH_2)_h$— where D is selected from H, CN, OH and C(O)OR, Y is selected from —N(R)—, —O—, —S(O)$_d$, —$CO_2$—, —CON(R)—, —N(R)CO—, C(R)=N— and a cyclic divalent moiety, preferably

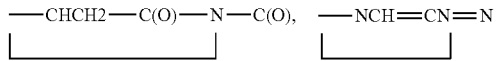

d is from 0 to 2, preferably 0, h is independently 0 to 4, preferably 2 or 3, m is independently 0 or 1, n is 0 to 4 and R is independently H, $C_{1-6}$ or phenyl, preferably H, methyl or ethyl;
ii) —$(CH_2)_hS(O)_d(CH_2)_n(Y)_m(CH_2)_h$ where Y is selected from —$CO_2$—, —CON(R)—, — and —N(R)CO—, h is independently 0 to 4, preferably 2 or 3, m is independently 0 or 1, n is independently 0 to 4 and d is from 0 to 2, preferably 0, and R is independently H, $C_{1-6}$ or phenyl, preferably H, methyl or ethyl; and
iii) —$(CH_2)_h$P(=O)(OR)O—$(CH_2)_h$ where h is independently 0 to 4, preferably 2 or 3.

In a preferred embodiment, the linking group L which links the $O_{3/2}Si$ silica group to group G has a chain of at least three atoms between the silica group and group G. Suitably, the linking group L has a chain length of not more than 15 atoms preferably 2 to 13 for example not more than 12 atoms between the silica group and group G. In an especially preferred embodiment, the linker group L comprises at least three parts, a —$CH_2CH_2$— bonded to the silica group, a link atom and optionally a connecting moiety. Preferably, the link atom is located at the third atom along the linker group from the silica group and is selected from carbon, oxygen, sulphur, phosphorus and nitrogen. Sulphur and carbon are especially preferred as link atoms. Groups L may be respectively referred to as carbon-linked, oxygen-linked, sulphur-linked, phosphorus-linked or nitrogen-linked depending on the link atom.

Preferably the linker group L is —$[CH_2CH_2S(O)_{0-2}]_{0-1}$ $[CH_2]_{0-3}[A1'']_{0-1}$- where A" is selected from:
- —NH(CO)—,
- —$CH(CH_2CO)(CO)NCH_2$—
- —N(CO)(CO) where group G comprises an aromatic ring and the carbonyl carbon atoms are bound directly to adjacent carbon atoms in the aromatic ring;
- —$N(CH_3)$—
- —$O(CO)_{0-1}$—

Examples of preferred carbon-linked groups L include —$(CH_2)_3$—, —$CH_2CH_2CHC((O)OCH_3)$—, —$CH_2CH_2CH(CN)$—, —$CH_2CH_2CH(CN)CONH(CH_2)_{1-4}$—, —$(CH_2)_{2-3}NHCO$—, —$(CH_2)_{2-3}CONH$—, $(CH_2)_3O(CH_2)_2CHOHCH_2NHCH_2$—, —$(CH_2)_3O(CH_2)_2CHOHCH_2S$—, and —$(CH_2)_3NHCH_2$—. Examples of preferred sulphur-linked groups include —$CH_2CH_2S$—$CH_2CH_2S(CH_2)_{1-4}SCH_2$—, —$CH_2CH_2S(CH_2)_{1-4}NHCO$—, —$CH_2CH_2SCH_2CONH(CH_2)_{0-2}$, —$CH_2CH_2S(CH_2)_2NH(CH_2)_{0-2}$—, —$CH_2CH_2S(CH)(CH_2CO)(CO)NCH_2$— and —$(CH_2)_2P(=O)(OR)O$—.

In combination with the preferred linker groups, group G is preferably ortho, meta or para bromophenyl.

The leaving group LG is suitably selected from a halide and a pseudohalide. The leaving group may be selected according to the particular reaction and catalyst with which the compound I is to be employed In preferred embodiments, where the catalyst to be bound comprises Pd, LG is Br, where the catalyst comprises Cu, LG is I and where the catalyst comprises Fe, LG is Cl. Where the catalyst comprises Ni, LG is suitably ester, nitrile or alkoxy, for example methoxy. In an especially preferred embodiment the aryl group G has a bromine substituent at the meta or para position of the benzene ring relative to the linker group L where group G is aryl.

In a preferred embodiment, substituent Q of group G is selected from H, $NR_2$, $N^+R_3$, —$N(R)CO_2H$, —$N=CR_2$, OR, —$O^+(R)SiR_3$, $CO_2R$, $CO_2^-$, $CONR_2$ $NRC(O)R$, F, Cl, $NO_2$, CN and a ring formed between group Q and a part of group L, for example —O—C(O)— where the ether oxygen is bound to G and the carbonyl group is a part of group L. Suitably, substituent Q is located at the ortho or meta position relative to linker group L where group G is aryl.

In another preferred embodiment, the aryl group G with substituent Q may be in equilibrium between two forms and, optionally may be derivatised. By selecting appropriate substituents Q, movement of the equilibrium may be affected by altering reaction conditions, for example pH or by adding a component so providing a means of controlling or tuning the position at which the equilibrium lies and controlling the level of binding or release of the catalyst.

Examples of preferred groups G with substituents Q which may be in equilibrium between two forms. Where Q is OH, it is preferably located at the ortho position and linker group L comprises a group which is capable of reversibly forming a ring with the OH substituent, preferably L comprises a pendant acid or ester group $CO_2R$ where the OH substituent and acid or ester group may form a ring. Where Q is $NR_2$, preferably NHR or $NH_2$, this group may reversibly form an ammonium ion $N^+H_3$ or $N^+R_3$ by altering the pH, or to —$N(R)CO_2H$ in the presence of free $CO_2$. Substituent Q may be —OR, preferably —$OCH_3$ and may be reversibly converted to —$O^+(R)$—$SiR_3$ in the presence of a trialkyl silane. Where substituent Q is $CO_2H$, changing the pH may reversibly convert this group to a carboxylate anion. Where R is $NH_2$, acetone or other carbonyl functionality may be added to derivatise the amine to the corresponding imines and for example in the case of acetone the reaction may be reversed by washing with water. By changing the reaction conditions, or introducing other components, group Q may exist in more than one form so enabling control of the position of the equilibrium.

In a fifth aspect, the invention provides for use of a compound of formula I, preferably a compound of formula VI to selectively remove a component from a reaction medium so the component may be treated and subsequently return the component to the reaction medium.

Suitably, the component to be removed from a reaction medium is one or more of a catalyst and unreacted feedstock. Unreacted feedstock typically is not subsequently returned to the reaction medium. In a preferred embodiment, the component to be removed comprises a metal with or without ancilliary ligands, more preferably a metal of Group 8, 9, 10 or 11 of the Periodic Table. Examples of preferred metals include palladium, platinum, rhodium, ruthenium, iridium, nickel, copper and iron, optionally comprising ancilliary ligands.

In a sixth aspect, the invention comprises an organometallic species of a catalyst CAT and a compound of formula I, preferably a compound of formula VI wherein CAT comprises a metal with or without ancilliary ligands. The catalyst CAT preferably comprises palladium, platinum, rhodium, iridium, ruthenium, copper, nickel or iron, optionally comprising ancilliary ligands. The catalyst CAT is preferably bound to the compound I at group G which has a substituent Q and a leaving group LG as hereinbefore defined. Preferably the catalyst CAT is interposed between the aryl, heteroaryl or alkyl group of group G and leaving group LG as shown in formula VII below:

[SUP]-[L]-[G][CAT]-[LG]

The compound for treating the species of formula VII is suitably of formula R""[MET]$_e$[X"]$_f$ (compound IV), as hereinbefore defined or a salt thereof, preferably an alkali metal salt M"X", for example R""B(OH)$_3^-$K$^+$) and after contacting with the compound of formula VII, the catalyst CAT is released into a reaction medium. Selectively removing the catalyst from the reaction medium allows feedstocks to be replenished or altered, impurities or by-products to be removed without the drawbacks associated with retaining a homogeneous catalyst in the reaction medium during such processing.

The catalyst CAT is suitably employed in a homogeneously catalysed process for the formation of a new carbon carbon, carbon nitrogen, carbon oxygen or other carbon heteroatom bond through a homogeneously catalysed process in which the catalyst may be selectively removed and returned to the reaction, the process involving the addition of a catalyst to a compound of formula R"-LG, wherein LG is a leaving group as hereinbefore defined, to produce an organometallic species of formula VIII R"-CAT-LG, treating the compound VIII whereby LG is replaced by a group selected from aryl, heteroaryl, benzyl, alkyl, vinyl, allyl, alkynyl, alkenyl, or heterocyclic moiety to provide a species of formula IX R"-CAT-R"" wherein R" and R"" are independently selected from aryl, heteroaryl, benzyl, alkyl, vinyl, allyl, alkynyl, alkenyl, or heterocyclic moiety.

The compound for treating the species of formula VIII is suitably of formula R""[MET]$_e$[X"]$_f$ as hereinbefore defined or a salt thereof and after contacting with the compound of formula VIII, the compound of formula IX and [MET]$_e$[X"]$_{f+1}$ is produced. The compound of formula IX may then be treated to release catalyst CAT into a reaction medium and to form compound R"—R"". The catalyst may then suitably be recovered from the reaction medium by binding with a compound of formula I or VI, thereby allowing the reaction medium to be treated for example to remove by-products, unreacted reactants and the like or to allow new reactants to be introduced or to alter reaction conditions in the absence of the catalyst. The captured catalyst may then be returned to the reaction medium as required.

Preferably LG is a halide or a pseudo halide as hereinbefore defined for example triflate, or under catalysis conditions with certain metals, an alkoxide, an ester and a nitrile.

We have found that the organopolysiloxanes of the invention are especially suited to recovery of metal catalysts employed in a wide range of reactions in which an aryl, vinyl, heterocyclic or alkyl boronic acid is reacted with an aryl, benzyl, alkyl, vinyl, allyl, alkynyl, alkenyl, acyl, sulfonyl or heterocyclic halide or pseudo halide catalyzed by a metal catalyst.

In a seventh aspect the invention provides a process for producing a reaction product by homogeneous catalysis comprising reacting a feedstock in the presence of a homogeneous catalyst in a reaction medium to produce directly or indirectly a reaction product, contacting the catalyst with a compound of formula I, preferably formula VI to remove the catalyst from the reaction medium to produce an organometallic species comprising the catalyst bound to the compound of formula I, preferably VI, treating the catalyst, returning the catalyst to the reaction medium and reacting a second feedstock in the presence of the returned homogeneous catalyst to produce a second reaction product or a second batch of the same reaction product.

The first and second feedstocks may be the same or different. For pharmaceutical preparation processes, the first and any subsequent feedstocks are advantageously the same, for regulatory reasons. With appropriate analysis and quality control, different feedstocks may be employed. Removal of the catalyst allows the catalyst life to be extended and the compound of formula I beneficially purifies the reaction product by removing excess feedstock as well as the catalyst to be regenerated from the reaction medium. The catalyst upon removal from the reaction medium is temporarily in heterogeneous form and is suitably released into the reaction medium by contact of the bound catalyst with the second feedstock.

The process of removing the catalyst from a reaction medium to form an organometallic species treating the species and reintroducing the catalyst into the same or a different reaction medium may be repeated as desired.

The process allows removal of excess reagent thereby improving product isolation.

In a further preferred aspect the invention provides a process for producing a reaction product comprising a coupled biaryl, aryl-heteroaryl, aryl-alkyl, heteroaryl-alkyl, biheteroaryl, bialkyl reaction product by homogeneous catalysis comprising reacting a feedstock comprising a compound of formula R""[MET]$_e$[X"]$_f$ or R""[MET]$_e$[X"]$_f^-$M"$^+$ with a compound of formula R"Br in the presence of a homogeneous catalyst comprising a metal in a reaction medium to produce a coupled biaryl product of formula R"—R"", contacting the catalyst with a compound of formula I, preferably a compound of formula VI as defined above to remove the catalyst from the reaction medium, treating the catalyst by contacting with a compound of formula R""[MET]$_e$[X"]$_f$ as hereinbefore defined to return it to the reaction medium and contacting the returned metal catalyst with a further feedstock to effect a further reaction to produce a second reaction product.

Suitably the catalyst may comprise any metal suitable for the reaction being carried out. Examples of suitable catalysts for treatment according to methods of the invention include Pt, Pd, Ni, Fe, Cu, Ir, Ru, Rh. The invention enables a metal catalyst to be removed from and reintroduced to a reaction medium together with any associated ancilliary ligands that may be present.

Suitably the catalyst may comprise Pd, Ni and Fe, especially for Suzuki reactions, Pd, Cu, Ni and Fe for formation of C—N and C—O bonds, Pd, Ni, Fe, Cu, Ir, Ru, Rh for formation of a C—C bond. Examples of suitable palladium catalysts include palladium combined with a phosphine including monodentate and bidentatephosphines, a phosphite, a phosphoramidite, a carbene, ligands containing nitrogen and ligands containing oxygen, and any combination of two or more of these groups. Examples of specific palladium catalysts include palladium acetate, bis(triphenylphosphine) palladium chloride or acetate and tetrakis(triphenylphosphine)palladium(0), include tris-dibenzylideneacetone di-palladium(0) plus other palladium ligand salts plus other metals.

The present invention enables catalysts to be removed from a wide-range of catalyzed reactions including alpha arylation (metal enolate), amidation, amination, etherification, esterification, cyanation (cyanide ion), and carbonylation reactions. Examples of particular reactions in which the present invention may be employed for catalyst removal and reintroduction include Miyaura borylation (pinacol borylation), Buchwald Hartwig amination (primary or secondary amine), Ullman etherification, Ullmann amination (Goldberg reaction), carbonylation for hydroformylation, ester, acid, amide and diketone formation, Chan Lam amination, Mizoroki Heck reaction (alkene), Sonogashira reaction (alkyne), Hiyama reaction (ArSi), Kumada Corriu reaction, Negishi reaction, reductive Heck Reaction, Tsuji Trost reaction (enolate), Stille reaction and Suzuki Miyaura reaction.

The process for producing a reaction product may be carried out in a batch process although a continuous process may be employed. Suitably the catalyst and feedstocks are fed to a reaction zone. The compound of the invention is suitably located in a separate bed, for example a conventional cartridge arrangement, in a recycle loop around the reaction zone. The reaction is carried out in the reaction zone, the reaction mixture is then passed through the separate bed and contacted with the compound of the invention. The catalyst and, as desired unreacted feedstocks are bound in the bed and the reaction mixture depleted in these components is fed elsewhere. A new feedstock, comprising the same or different components to those previously employed or coupling partner is then passed through the bed and releases the catalyst from the bed and is carried back to the reaction zone where the second or subsequent reaction is carried out.

Where compound I or VI comprises a silica or alumina support, silicas and aluminas suitable for functionalization to produce a compound of formula I or VI include any silica or alumina having surface Si(OH) or Al(OH) moieties respectively. The silica or alumina may be produced by treating a commercially available silica or alumina with alkenyl trialkoxysilane, for example vinyl trimethoxy silane available from Sigma Aldrich (cat no. 235768). Sulphur-linked compounds may be produced by treating with a thiol under radical generating conditions to afford a sulphur-linked compound of formula I or VI. A functionalised trialkoxysilane may be produced by reacting with a species to produce the desired functional group and which is then coated on or reacted with an existing support of silica or alumina.

Where compound I or VI comprises a polymer, for example polystyrene support, copolymerisation of a commercially available functionalised monomer for example a functionalised styrene with a monomer, for example styrene, with or without copolymer additives, using standard techniques affords the functionalised polymer support. Alternatively functionalization of a pre-formed polymer may also be employed using conventional methods.

The invention is now illustrated by the following illustrative examples.

EXAMPLE 1

Production of 4-Bromophenyl amidoethyl sulfide ethyl silica

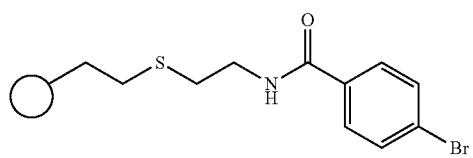 [SMILES: CCCSCCNC(=O)c1ccc(Br)cc1]

Cysteamine hydrochloride (193.10 g, 1.7 mol) was stirred and heated to 120° C. When the material had become molten, vinyl trimethoxysilane (229.95 g, 1.55 mol) and tert-butyl peroxide (2.0 mL, 10.89 mmol) was added over 30 min. The heterogeneous mixture was heated at 120-130° C. for a further hour, before a second addition of tert-butyl peroxide (2.0 mL, 10.9 mmol). The reaction mixture was stirred for 2 hours at this temperature whereupon the solution had become homogeneous. The solution was then cooled to room temperature to provide a crude product.

A mixture of this crude product above, silica (1.00 kg, 70-230 mesh) and toluene (2.5 L) was heated at reflux for 4 h. After cooling, the reaction mixture was filtered and washed with toluene, methanol and water before being dried on the sinter funnel until mobile. A mixture of the semi-dried material and water (2 L) was stirred and a pH probe was carefully immersed in the solution. Sodium hydroxide solution (853 mL, 1.5 M) was added over 10 minutes. The solution pH was monitored during the addition and requires an end-point of pH 8.8-9.2. The mixture is stirred for a further 20 minutes then filtered, washed with water and methanol and dried in a vacuum oven. The structure was verified by NMR techniques.

A mixture of 4-bromobenzoic acid (1.2 g, 6 mmol, 1.05 eq. based on functional group (FG) loading and DMF (15 mL) was stirred for 5 min at room temperature to afford a colourless solution. Diisopropylamine (1.05 eq. based on FG loading) followed by O-(Benzotriazol-1-yl)-N,N,N',N'-tetramethyluronium hexafluorophosphate (1.6 g, 6 mmol, 1.05 eq. based on FG loading) are added at 5 min intervals with continual stirring. After a further 5 min, the product from above (5.0 g) is added and stirring continued for 1 h, whereupon the reaction mixture is filtered and washed with methanol, 1 M aqueous $Na_2CO_3$, water and methanol and dried. The structure was verified by NMR techniques.

EXAMPLE 2A

Production of 4-Bromophenyl amidopropyl silica

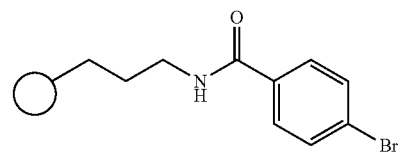

Silica (50 g, 70-200 micron, 60 Å), 3-aminopropyl trimethoxysilane (11.2 g, 62.5 mmol) and toluene (140 mL) were heated at reflux for 4 h. The reaction was then allowed to cool and was filtered. The solid was washed with methanol and dried in a vacuum oven.

4-Bromobenzoic acid (1.21 g, 6 mmol) and DMF (15 mL) were stirred for 5 minutes at room temperature to afford a colourless solution. Diisopropylamine (1.58 g, 6 mmol) followed by O-(Benzotriazol-1-yl)-N,N,N',N'-tetramethyluronium hexafluorophosphate (2.28 g, 6 mmol) were added at 5 min intervals with continual stirring. After a further 5 min 3-aminopropyl functionalised silica (from above) (5.00 g, 1.25 mmol/g functional group loading) is added and stirring continued for 1 h whereupon the reaction mixture is filtered and the silica washed with methanol, water, 1 M aqueous $Na_2CO_3$, water and methanol and dried in a vacuum oven. The structure was verified by NMR techniques.

EXAMPLE 2B

Production of 4-Bromophenyl amidopropyl silica

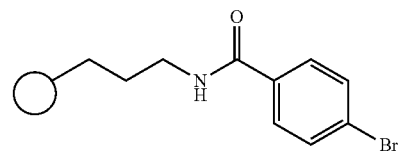

A solution of benzoic acid (2.11 g, 10.5 mmol) and DMF (25 mL) was stirred at room temperature for 5 min. Triethylamine (2.00 g, 20.0 mmol) was added and the stirring continued at room temperature, after 5 min HBTU (3.98 g, 10.5 mmol) was added, followed 5 min later by aminopropyl trimethoxysilane (1.79 g, 10.0 mmol). The reaction mixture was shaken at room temperature for a further 1 h.

A mixture of the crude product above, silica (10.00 g, 70-230 mesh) and toluene (50 mL) was heated at reflux for 4 h. After cooling, the reaction mixture was filtered and washed with toluene and methanol before being dried. The structure was verified by NMR techniques.

EXAMPLE 3

Production of Bromophenyl silica

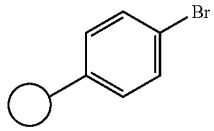

A mixture of bromophenyltrimethoxysilane (1.00 g, 3.6 mmol), silica (5.00 g, 70-230) and toluene (20 mL) was heated at reflux for 4 h. After cooling, the reaction mixture was filtered and washed with toluene and before being dried. The structure was verified by NMR techniques.

EXAMPLE 4

Production of 4-Bromophenyl sulfide ethyl Silica

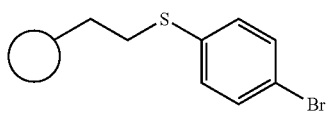

A mixture of trimethoxyvinylsilane (1.48 g, 10.0 mmol), 4-bromothiophenol (2.27 g, 12.0 mmol), AIBN (0.08 g) and toluene (10 mL) was heated to 50° C. The temperature was maintained for 6 h, with AIBN (0.08 g) being added hourly and further 4-bromothiophenol (1.14 g, 6.0 mmol) being added after 3 h.

A mixture of the crude product above, silica (10.00 g, 70-230 mesh) and toluene (50 mL) was heated at reflux for 4 h. After cooling, the reaction mixture was filtered and washed with toluene and methanol before being dried. The structure was verified by NMR techniques.

EXAMPLE 5

Production of 3-Bromobenzyl succinimido sulfide ethyl silica

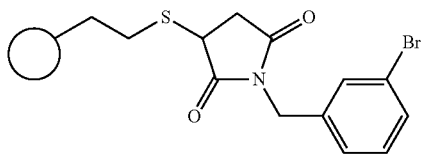 [SMILES: CCCSC1CC(=O)N(Cc2cccc(Br)c2)C1=O]

Mercaptosuccinic acid (99.87 g, 0.67 mol) was heated until an internal pot temperature of 80° C. is reached, then a solution of vinyl trimethoxysilane (81.34 g, 0.59 mol) and di tert butyl peroxide (1.74 mL, 9.5 mmol) was added dropwise. The mixture was heated for a further 2 hours, reaching a temperature of 105° C. A further addition of di tert butyl peroxide (1.74 mL, 9.5 mmol) was made and the mixture refluxed for a further hour. Once satisfied (by proton NMR sample analysis) that the reaction was complete, methanol (120 mL) was added and the material cooled to room temperature.

Silica (0.38 kg, 70-200 μm, 60 Å) toluene (1.0 L) and material from Step 1 (0.59 mol) were heated at reflux for 4 h. The reaction was then allowed to cool and the solid material was washed with methanol, sodium hydroxide, water and methanol and then dried on the sinter funnel until mobile.

3-Bromobenzylamine hydrochloride (8.90 g, 40 mmol), aqueous sodium carbonate solution (50 mL, 1 M) and toluene (50 mL) were stirred and heated to approx. 100° C. for 1 h (or until all solid has dissolved) whereupon the mixture was allowed to cool and the phases separated. The organic phase was then added to a mixture of succinic acid ethyl sulphide silica (29 g, 1.4 mmol/g loading), methane sulfonic acid (0.19 g, 2 mmol) and toluene (50 mL). The resultant mixture was heated at reflux under Dean-Stark conditions for 4 h before being allowed to cool. The solid was filtered and washed with toluene and methanol and dried in a vacuum oven. The structure was verified by NMR techniques.

EXAMPLE 6

Production of 2-Bromophenyl sulfide ethyl Silica

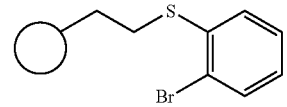

A mixture of trimethoxyvinylsilane (1.48 g, 10.0 mmol), 2-bromothiophenol (2.27 g, 12.0 mmol), AIBN (0.08 g) and toluene (10 mL) was heated to 50° C. The temperature was maintained for 6 h, with AIBN (0.08 g) being added hourly and further 2-bromothiophenol (1.14 g, 6.0 mmol) being added after 3 h.

A mixture of the resulting crude product above, silica (10.00 g, 70-230 mesh) and toluene (50 mL) was heated at reflux for 4 h. After cooling, the reaction mixture was filtered and washed with toluene and methanol before being dried. The structure was verified by NMR techniques.

EXAMPLE 7

Production of 3-Bromophenyl sulfide ethyl Silica

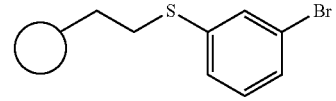

A mixture of trimethoxyvinylsilane (1.48 g, 10.0 mmol), 3-bromothiophenol (2.27 g, 12.0 mmol), AIBN (0.08 g) and toluene (10 mL) was heated to 50° C. The temperature was maintained for 6 h, with AIBN (0.08 g) being added hourly and further 3-bromothiophenol (1.14 g, 6.0 mmol) being added after 3 h.

A mixture of the resulting crude product above, silica (10.00 g, 70-230 mesh) and toluene (50 mL) was heated at reflux for 4 h. After cooling, the reaction mixture was filtered and washed with toluene and methanol before being dried. The structure was verified by NMR techniques.

EXAMPLE 8

Production of 4-Chlorophenyl sulfide ethyl Silica

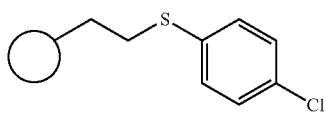

A mixture of trimethoxyvinylsilane (1.48 g, 10.0 mmol), 4-chlorothiophenol (2.17 g, 15.0 mmol), AIBN (0.08 g) and toluene (10 mL) was heated to 50° C. The temperature was maintained for 6 h, with AIBN (0.08 g) being added hourly and further 4-chlorothiophenol (1.00 g, 7.0 mmol) being added after 3 h.

A mixture of the resulting crude product above, silica (10.00 g, 70-230 mesh) and toluene (50 mL) was heated at reflux for 4 h. After cooling, the reaction mixture was filtered and washed with toluene and methanol before being dried. The structure was verified by NMR techniques.

EXAMPLE 9

Production of 4-Bromophenyl sulfoxide ethyl Silica

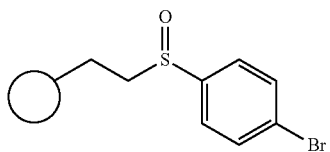

A mixture of the product from Example 4 (1.00 g) and DCM (14 mL) was cooled in an ice-bath and mCPBA (1.0 eq. based on FG loading) was added with stirring. The mixture was allowed to warm to room temperature over 2 h before being filtered and washed with toluene and methanol and then dried. The structure was verified by NMR techniques.

EXAMPLE 10

Production of 4-Bromophenyl sulfone ethyl Silica

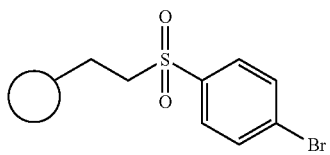

A mixture of the product from Example 4 (5.00 g) and DCM (14 mL) was cooled in an ice-bath and mCPBA (4.0 eq. based on FG loading) was added with stirring. The mixture was allowed to warm to room temperature over 2 h before being filtered and washed with toluene and methanol and then dried. The structure was verified by NMR techniques.

EXAMPLE 11

Production of N-(4-Bromophenyl)-N-methyl aminopropyl Silica

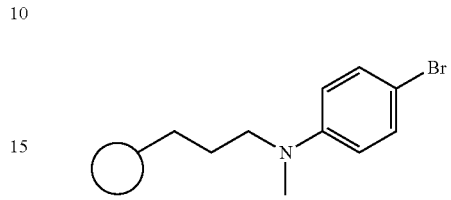

A mixture of chloropropyl trimethoxysilane (1.99 g, 10.0 mmol), 4-bromo-N-methyl aniline (4.65 g, 25.0 mmol), sodium bromide (1.13 g, 11.0 mmol) and DMF (10 mL) was heated to 100° C. and stirred at that temperature for 17.5 h.

A mixture of the resulting crude product above, silica (10.00 g, 70-230 mesh) and toluene (50 mL) was heated at reflux for 4 h. After cooling, the reaction mixture was filtered and washed with toluene and methanol before being dried. The structure was verified by NMR techniques.

EXAMPLE 12

Production of 4-Bromobenzoate propyl Silica

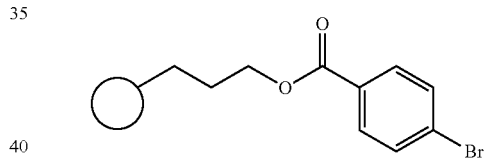

A mixture of 4-bromobenzoic acid (4.02 g, 20.0 mmol), cesium carbonate (3.26 g, 10.0 mmol) and DMF (10 mL) was heated to 50° C. for and stirred for 30 min. Sodium bromide (1.23 g, 12.0 mmol), chloropropyltrimethoxysilane (1.99 g, 10.0 mmol) and DMF (10 mL) were then added and the resultant mixture heated at 80° C. for 16 h.

A mixture of the resulting crude product above, silica (10.00 g, 70-230 mesh) and toluene (50 mL) was heated at reflux for 4 h. After cooling, the reaction mixture was filtered and washed with water and methanol before being dried. The structure was verified by NMR techniques.

EXAMPLE 13

Production of 4-Bromophenyl ethyl Silica

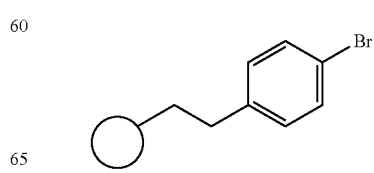

A mixture of trimethoxy(2-phenylethyl)silane (0.50 g, 2.2 mmol) and DCM (5 mL) was cooled in an ice bath and bromine (1.40 g, 8.8 mmol) was added dropwise. The resultant mixture was stirred and allowed to warm to room temperature over 1 h before being diluted with DCM (5 mL) and partitioned with aqueous $Na_2S_2O_7$ solution (10 mL, 1 M). The organic phase was separated and washed with water (10 mL) and brine (20 mL), toluene (10 mL) was then added and the DCM removed in vacuo.

A mixture of the resulting crude product above, silica (10.00 g, 70-230 mesh) and toluene (50 mL) was heated at reflux for 4 h. After cooling, the reaction mixture was filtered and washed with toluene and methanol before being dried. The structure was verified by NMR techniques.

EXAMPLE 14

Production of 4-Bromophenoxy propyl functionalised Silica

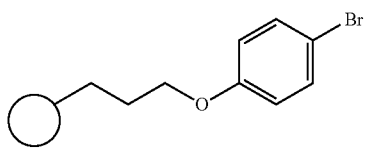

A mixture of chloropropyl trimethoxysilane (1.99 g, 10.0 mmol), sodium iodide (1.80 g, 12.0 mmol) and DMF (10 mL) was heated to 50° C. for 1.5 h. 4-Bromophenol (5.19 g, 30.0 mmol), potassium carbonate (2.07 g, 15.0 mmol) and DMF (10 mL) were then added and the resultant mixture heated at 80° C. for 22.5 h.

A mixture of the resulting crude product above, silica (10.00 g, 70-230 mesh) and toluene (50 mL) was heated at reflux for 4 h. After cooling, the reaction mixture was filtered and washed with water and methanol before being dried. The structure was verified by NMR techniques.

EXAMPLE 15

Production of 4-Bromophenyl sulfide ethyl; propyl functionalised Silica

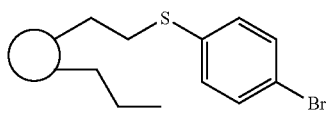

A mixture of the product from Example 4, trimethoxypropyl silane (1.0 mmol/g silica input) and toluene (3.5 mL/g silica, or minimum 50 mL) was heated at reflux for 4 h. After cooling, the reaction mixture was filtered and washed with toluene and methanol before being dried. The structure was verified by NMR techniques.

EXAMPLE 16

Production of Bromophthalimido propyl functionalised Silica

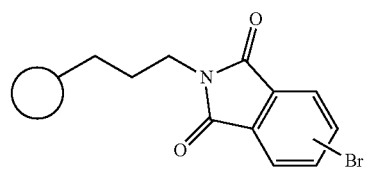

A mixture of chloropropyl trimethoxysilane (1.99 g, 10.0 mmol), phthalimide (3.68 g, 25.0 mmol), caesium carbonate (3.58 g, 11.0 mmol), sodium bromide (1.13 g, 11.0 mmol) and DMF (10 mL) was stirred and heated to 55° C. for 16 h.

A mixture of the resulting crude product from above, silica (10.00 g, 70-230 mesh) and toluene (50 mL) was heated at reflux for 4 h. After cooling, the reaction mixture was filtered and washed with water and methanol before being dried. The structure was verified by NMR techniques.

A mixture of the product from above (6.00 g) and DCM (30 mL) was cooled to 0° C. and bromine (1.0 eq. based on FG loading) added dropwise. The reaction mixture was allowed to warm to room temperature over 4 h before being filtered and washed with DCM, water and methanol before being dried. The structure was verified by NMR techniques.

EXAMPLE 17

Phenyl 4-trifluoromethanesulfonate sulfide propyl functionalised Silica

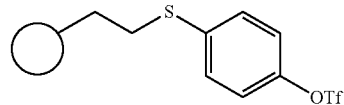 [SMILES: CCCSc1ccc(OS(=O)(=O)C(F)(F)F)cc1]

A mixture of chloropropyl trimethoxysilane (3.62 g, 18.0 mmol), thiophenol (5.75 g, 46.0 mmol), sodium bromide (2.06 g, 20.0 mmol), potassium carbonate (3.78 g, 27.0 mmol) and DMF (18 mL) was stirred and heated to 100° C. for 18 h.

A mixture of the resulting crude product from above, silica (22.00 g, 70-230 mesh) and toluene (80 mL) was heated at reflux for 4 h. After cooling, the reaction mixture was filtered and washed with water and methanol before being dried. The structure was verified by NMR techniques.

A mixture of the product from above (8.00 g), 4-nitrophenyl trifluoromethanesulfonate (1.0 eq. based on FG loading), potassium carbonate (1.0 eq. based on FG loading) and DMF (25 mL) was stirred at room temperature for 4 h before being filtered and washed with water and methanol before being dried. The structure was verified by NMR techniques.

EXAMPLE 18

Preparation of Supported Palladium Catalyst

A sample of Palladium (bis(di-tert-butylphosphin)ferrocene)dichloride (1 mmol) was dispensed to a reaction tube.

Phenyl boronic acid (3 mmol) and potassium carbonate (3 mmol) were added. The supported Aryl Br produced in Example 3 was added (5 mmol). Acetonitrile (20 rel volumes) and water (5 rel volumes) were added to the reaction mixture. The reaction was stirred and heated to 60° C. The reaction was analysed by GCMS after 1 h showing complete consumption of phenylboronic acid. The supported Aryl Br contained the colour and the solvent was a very light yellow colour. The catalyst is coloured and the colour comes out of solution onto the supported aryl bromide. Upon washing the support, catalyst is released and the support is usable in a new reaction.

EXAMPLE 19

Removal of Palladium from a Suzuki Reaction

A sample of Palladium (bis(di-tert-butylphosphin)ferrocene)dichloride (0.05 mmol) was dispensed to a reaction tube. 4-Bromobenzonitrile (1 mmol), phenyl boronic acid (1.1 mmol) and potassium carbonate (1.1 mmol) were added. Acetonitrile (5 rel volumes) and water (5 rel volumes) were added to the reaction mixture. The reaction was stirred and heated to 60° C. The reaction was analysed by GCMS after 18 h showing complete consumption of 4-bromobenzonitrile. The supported Aryl Br produced in Example 3 was added (0.5 mmol) and the mixture stirred at 60° C. overnight. The supported Aryl Br contained the colour and the solvent was a very light yellow colour.

EXAMPLE 20

Use of Supported Palladium Catalyst for Suzuki Reaction

4-Bromobenzonitrile (1 mmol), phenyl boronic acid (1.1 mmol) and potassium carbonate (1.1 mmol) were added to a reaction tube. Acetonitrile (5 rel volumes) and water (5 rel volumes) were added to the reaction mixture. The supported aryl bromide produced in Example 18 with attached Pd ligand organometallic species was added to the reaction. The reaction was stirred and heated to 60° C. The reaction was analysed by GCMS after 18 h showing complete consumption of 4-bromobenzonitrile. The supported Aryl Br was added (0.5 mmol) and the mixture stirred at 60° C. overnight. The supported Aryl Br contained the colour and the solvent was a very light yellow colour, the catalyst being coloured. The support may be washed to release the catalyst and then reused as desired.

The invention claimed is:
1. A process for the selective removal of a soluble catalyst component from a reaction medium and subsequently returning the soluble catalyst component to a reaction medium comprising contacting a compound of formula I below with a first reaction medium to bind the soluble catalyst component to the Compound I thereby forming a bound component, separating the bound component and the first reaction medium, subsequently returning the bound catalyst component to a second reaction medium in which the bound component undergoes a reaction whereby the soluble catalyst component is released from Compound I wherein the Compound I is of formula:

$$[SUP]\text{-}[[L]\text{-}[G]]_{n'} \quad (I)$$

wherein:
L is a group linking G to SUP- of formula:
—$(CH_2)_h[S(O)_d]_m(CHD)_nZ_m((CH_2)_nY(CH_2)_n)_m$ where D is selected from H, CN, OH, —C(O)OR, —C(O)NR_2, —C(O)OG, —CONRG and Y is selected from O, NR, $S(O)_d$, CO, $CO_2$, —$NRCOZ_m$—, —$Z_m$-CONR—, —C=N—, a heterocyclic ring where Z is independently O, S, NR;
and wherein d is independently 0 to 2, h is from 0 to 15, m is independently 0 or 1 and n is independently 0 to 4 and R is independently selected from H or a $C_{1-12}$ alkyl group and a phenyl group; or L is not present and G is linked directly to SUP;
G is selected from an alkyl group, an aryl group, a heterocyclic group and a heteroaryl group wherein the group G has
a. a leaving group LG selected from Cl, Br, I and a pseudohalide; and
b. substituent Q selected from H, $NR_2$, $N^+R_3$, —N(R)$CO_2H$, —N=$CR_2$, OR, —$O^+(R)SiR_3$, $CO_2R$, $CO_2^-$, —$CONR_2$, —NRC(O)R, F, Cl, $NO_2$, CN and a ring formed between group Q and a part of group L;
SUP is a support having a plurality n' of groups -[L]-[G] bound to the support.
2. A process according to claim 1 wherein the support SUP is selected from a polymer, silica and alumina.
3. A process according to claim 1 wherein the Compound I is an organopolysiloxane wherein the support SUP comprises silica and group G is an optionally substituted haloaryl, haloheteroaryl or haloalkyl group.
4. The process according to claim 1, wherein h is from 0 to 4 and G is selected from an alkyl group, an aryl group and a heteroaryl group.
5. A process for the selective removal of a catalyst component from a reaction medium and subsequently returning the catalyst component to a reaction medium comprising contacting a compound of formula IA below with the reaction medium to bind the catalyst component to the Compound IA thereby forming a bound component, separating the bound component and the reaction medium, subsequently returning the bound component to a reaction medium and treating the bound component so as to release the catalyst component from Compound IA wherein the Compound IA is of formula:

$$[SUP]\text{-}[G]_{n'} \quad (IA)$$

wherein G is linked directly to SUP;
G is selected from an alkyl group, an aryl group, a heterocyclic group and a heteroaryl group wherein the group G has
i) a leaving group LG selected from Cl, Br, I and a pseudohalide; and
ii) substituent Q selected from H, $NR_2$, $N^+R_3$, —N(R)$CO_2H$, —N=$CR_2$, OR, —$O^+(R)SiR_3$, $CO_2R$, $CO_2^-$, —$CONR_2$ —NRC(O)R, F, Cl, $NO_2$ and CN;
SUP is a support having a plurality n' of groups -[G] bound to the support.

* * * * *